(12) United States Patent
Herloski et al.

(10) Patent No.: US 7,544,923 B1
(45) Date of Patent: Jun. 9, 2009

(54) LED SIGNATURE ELIMINATION IN SPECULAR-MODE LED ILLUMINATION HAVING A LIGHT DIFFUSER BETWEEN AN ILLUMINATOR ARRAY AND AN IMAGE BEARING SURFACE

(75) Inventors: Robert Herloski, Webster, NY (US); Douglas Proctor, Rochester, NY (US); John Juhasz, Fairport, NY (US); Eric Dudley, Rochester, NY (US)

(73) Assignee: Xerox Corporation, Norwalk, CT (US)

( * ) Notice: Subject to any disclaimer, the term of this patent is extended or adjusted under 35 U.S.C. 154(b) by 13 days.

(21) Appl. No.: 12/020,106

(22) Filed: Jan. 25, 2008

(51) Int. Cl.
*H01J 3/14* (2006.01)
(52) U.S. Cl. .................... 250/216; 250/208.1
(58) Field of Classification Search .......... 250/208.1, 250/216, 234, 235, 559.4, 559.17; 399/52, 399/220, 128, 49, 221, 177; 358/471–475, 358/484; 355/41–70; 362/16, 26, 310, 606–610
See application file for complete search history.

(56) References Cited

U.S. PATENT DOCUMENTS 4,967,238 A * 10/1990 Bares et al. .................. 399/34
6,975,949 B2  12/2005 Mestha et al.

\* cited by examiner

*Primary Examiner*—Que T Le
(74) *Attorney, Agent, or Firm*—Pillsbury Winthrop Shaw Pittman LLP

(57) ABSTRACT

A system for detecting reflectance from an image bearing surface in a printer or electronic copier includes an illuminator array, positioned adjacent to the image bearing surface, comprising a plurality of discrete illuminator elements that are spaced in a linear arrangement; a light diffuser positioned between the illuminator array and the image bearing surface, the light diffuser being positioned with respect to the illuminator array to receive the light beams emitted by the illuminator elements and to diffuse the light beams for transmission to the image bearing surface at an incidence angle; and a linear sensor array positioned adjacent to the image bearing surface such that specular and diffuse portions of the light beams reflecting off the image bearing surface at a reflectance angle bearing are received by the sensors.

14 Claims, 12 Drawing Sheets

LED SIGNATURE ELIMINATION IN SPECULAR-MODE LED ILLUMINATION HAVING A LIGHT DIFFUSER BETWEEN AN ILLUMINATOR ARRAY AND AN IMAGE BEARING SURFACE

FIELD

The present disclosure relates to a system for providing specular reflectance of an image bearing surface in a printer.

BACKGROUND

Defects in the subsystems of a xerographic, electrophotographic or similar image forming system, such as a laser printer, digital copier or the like, may give rise to visible streaks in a printed image. Streaks are primarily one-dimensional defects in an image that run parallel to the process (or slow scan) direction. In a printing system, an image input module is used to measure reflection from an image bearing surface and from test patches on the image bearing surface. These image input modules are often referred to as densitometers, as they detect the density or lack thereof of toner on the image bearing surface. These measured reflections are used in a streak correction methodology in the printer.

In prior systems, the image input module uses a fluorescent or a rare gas lamp for illuminating the image bearing surface and the test patches. The fluorescent or the rare gas lamp used for illumination is a continuous source of light in the cross-process (or fast scan) direction. However, the fluorescent or the rare gas lamp is relatively expensive.

SUMMARY

In an embodiment, a system for detecting reflectance from an image bearing surface in a printer or electronic copier is provided. The system includes an illuminator array, a light diffuser, and a linear sensor array. The illuminator array, positioned adjacent to the image bearing surface, includes a plurality of discrete illuminator elements spaced in a linear arrangement, where the illuminating elements are each configured to emit a light beam for transmission to the image bearing surface at an incidence angle. The light diffuser is positioned between the illuminator array and the image bearing surface. The light diffuser is positioned with respect to the illuminator lens to receive the light beams emitted by the illuminator elements and to diffuse the light beams being transmitted to the image bearing surface in the linear direction of the illuminator array. The linear sensor array includes a plurality of sensors positioned adjacent to the image bearing surface such that specular and diffuse portions of the light beams reflecting off the image bearing surface at a reflectance angle are received by the sensors.

In another embodiment, a method for detecting reflectance from an image bearing surface in a printer or electronic copier is provided. The method includes positioning an illuminator array with a plurality of discrete illuminator elements spaced in a linear arrangement adjacent to the image bearing surface and configuring the illuminator elements to emit a light beam for transmission to the image bearing surface at an incidence angle; positioning a light diffuser between the illuminator array and the image bearing surface; positioning the light diffuser with respect to the illuminator array to receive the light beams emitted by the illuminator elements and to diffuse the lights beams being transmitted to the image bearing surface in a linear direction of the illuminator array; positioning a linear sensor array comprising a plurality of sensors adjacent to the image bearing surface, such that specular portions and diffuse portions of the light beams reflecting off the image bearing surface at a reflectance angle are received by the sensors.

Other aspects, features, and advantages will become apparent from the following detailed description, and the accompanying drawings.

BRIEF DESCRIPTION OF THE DRAWINGS

Various embodiments will now be disclosed, by way of example only, with reference to the accompanying schematic drawings in which corresponding reference symbols indicate corresponding parts, in which.

DETAILED DESCRIPTION

Figure 1:
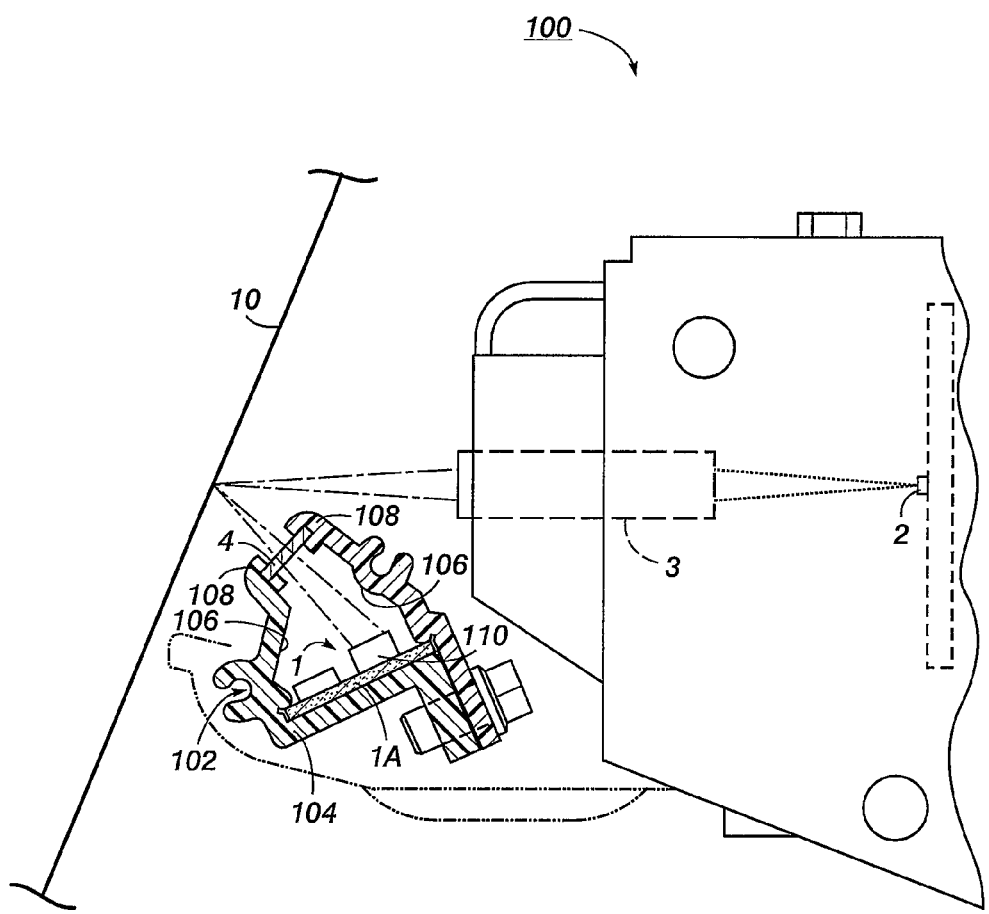
FIG. 1 is a cross-sectional view of an image input module (including the LED illumination system) used in a printer and an image bearing surface.

The law of reflection states that the direction of a specular component of the outgoing reflected light and the direction of incoming light make the same angle with respect to the surface normal. That is, the angle of incidence is equal to the angle of reflectance. Specular reflection is the mirror-like reflection of light from a surface, in which light from a single incoming direction is reflected into a single outgoing direction. In contrast, diffuse reflection is reflection of light from a surface, in which light from a single incoming direction is reflected in many directions, due to surface irregularities that cause the rays of light to reflect in different outgoing directions. The type of reflection depends on the structure of the surface. For example, in a printer, the area on the image bearing surface that is covered by the toner exhibits a higher proportion of diffuse reflection, while the area on the image bearing surface that is not covered by the toner exhibits a higher proportion of specular reflection.

An image input module in a printer measures reflections from an image bearing surface and from the test patches on the image bearing surface. Test patches are predetermined patches of toner periodically transferred to the image bearing surface for calibration purposes. By imaging the test patches, the printer can evaluate each printed test patch against its optimal characteristics, and make adjustments to the toner deposition functionality of its print engine accordingly. The image input module may use these reflections in the streak correction methodology of the printer.

The printer generally has two important dimensions: the process (or slow scan) direction and the cross-process (or fast scan) direction. The direction in which the image bearing surface moves is referred to as process (or slow scan) direction, and the direction in which the plurality of sensors are oriented is referred to as cross-process (or fast scan) direction. The cross-process (or fast scan) direction is generally perpendicular to the process (or slow scan) direction.

The image input module comprises an illuminator array, a lens (such as a self-focusing gradient index lens, e.g., a Selfoc® lens) and an image sensor. The angular distribution of light produced by the illuminator at the image bearing surface can vary in the fast scan direction, depending upon the illuminator architecture, particularly in the case of discrete light sources such as LEDS. Under specular conditions, the light received by the image sensor depends upon the angular acceptance angle of the imaging lens. The angular acceptance angle of the imaging lens can be expressed as $\pm\alpha$, where $\alpha$ may be 5°, 10°, or other predefined angle which is a fixed property of the lens. In general, light that is incident at an angle of $\leq \pm\alpha$ relative to the normal to the image bearing surface (in the fast scan direction) will, under specular reflection conditions, be reflected at an angle of $\leq \pm\alpha$ relative to the optical axis of the imaging lens and will be captured by the imaging lens and transmitted to the image sensor. Light outside that range of angles will not be transmitted by the lens. At the fast scan locations above, or nearly above, an LED, there is a significant portion of light with an angular distribution within the acceptance angle of the lens, and the specularly reflected light is transmitted to the image sensor. However, between LEDs, if the gap is large enough, the only light incident on the image bearing surface has an angular distribution greater than the acceptance angle of the lens, and hence is not transmitted to the image sensor.

By modifying the angular distribution of light from the light source(s), the quantity of light collected by the imaging lens is substantially the same at every location in the cross-process (fast scan) direction, independent of whether one is over an LED or in between LEDs.

In addition, the image input module is sensitive to the uniformity of the illumination. Since the image input module measures both the specular reflection from the image bearing surface, which is an indication of the area that is not covered by the toner, and the diffuse reflection from the toner on the image bearing surface, which is an indication of the area that is covered by the toner, an important parameter to detect is the nonuniformity of the specular to diffuse ratio (on a pixel by pixel basis). The specular reflectance from the image bearing surface is the desired signal in these measurements while the diffuse reflectance from the toner on the image bearing surface is an unwanted signal. Therefore, to maximize the specular component in relation to the diffuse component in the optical system of the image input module, the uniformity of the illumination in the plane of the illuminator array has to be improved.

The specular reflectance is also particularly useful for the halftone masking of the image bearing surface. Halftone technique simulates continuous tone imagery through the use of equally spaced dots of varying size. In halftone techniques, the density of colored dots (typically the four colors, cyan, magenta, yellow and black), within an area is varied to reproduce any particular shade. Therefore with halftone, the patches have dots with toner and blank areas between these dots. If the patches are more dense, i.e., more dots per area coverage, then the specular signal received from the image bearing surface, which is an indication of the blank areas that is not covered by the toner, is weaker. On the other hand, if the patches are less dense, i.e., less dots per area coverage, then the specular signal received from the image bearing surface, which is an indication of the blank areas that is not covered by the toner, is stronger. As discussed earlier, high specular reflectance represents the blank areas between the dots (as the image bearing surface has a high specular reflectance).

The uniformity of the illumination in the plane of the illuminator array, and particularly in its linear direction, is improved by using a light diffuser to create a curtain of light essentially homogenized in the direction of the image bearing surface. The diffuser helps to insure more uniform specular image capture. The diffuser transforms divergent beams of the light from an illuminator array into a homogenized light with high-transmission efficiency.

Figure 2:
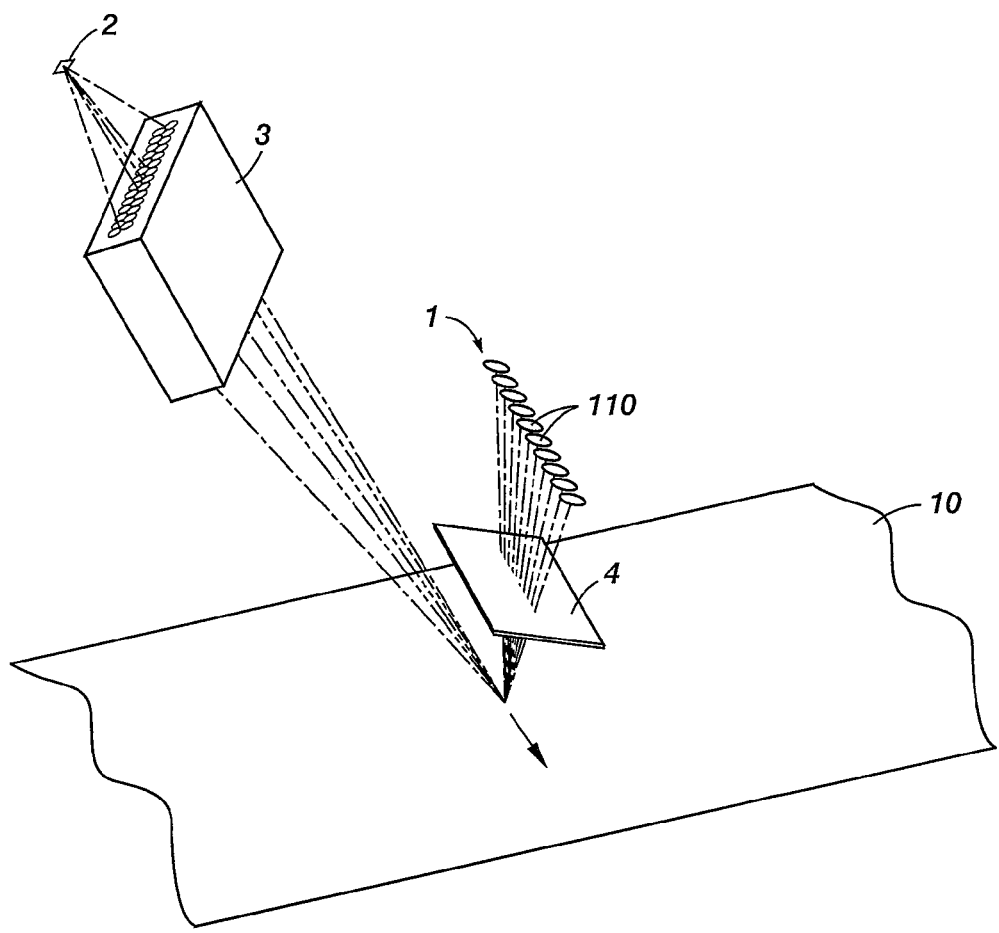
FIG. 2 is a perspective view of the image input module (including the LED illumination system) used in a printer and the image bearing surface.

FIGS. 1 and 2 show an LED illumination system for a specular-mode imager using a light diffuser. The system includes an illuminator array 1, a light diffuser 4, an image input module 100 with a lens array 3, and a sensor array 2.

The illuminator array 1 has a plurality of discrete illuminator elements 110 that are spaced in a linear arrangement within a housing 102. The housing 102 of the LED illumination system accommodates the LEDs and surrounds them. The LEDs are placed on a board 1A on the base 104 of the housing 102. A pair of arms 106 extends from the base 104 of the housing 102 encapsulating the LEDs there within. The light diffuser 4 is disposed in a recess 108 located on each of the pair of arms 106. The LED illumination system thus allows light from the LEDs to exit through the housing 102 containing the diffuser 4, achieving highly uniform diffusion and light emission from the LEDs, thereby obtaining a highly uniform light source. As such, the specular to diffuse ratio of the light beam exiting the diffuser can be highly uniform along the length of the illuminator array, despite the presence of the gaps between the LEDs.

Preferably, the illuminator elements of the illuminator array 1 are LEDs that are equally spaced at regular intervals. In an embodiment, the LEDs are spaced about every 4 mm apart in the fast scan direction. In another embodiment, the linear LED array could also use more than one row of LEDs. The combination of a linear array sensor and linear LED array allows for high spatial resolution (e.g., 600 spots per inch) in both the slow scan and fast scan directions. In one embodiment, the LED arrays could be all one color, e.g., white or of multiple colors, as described in U.S. Pat. No. 6,975,949, incorporated herein by reference. Other discrete light sources are also contemplated, such as fiber optic light guide tubes.

In an embodiment, the image bearing surface 10 used in the system is on a photoreceptor comprising a belt or a drum configuration. However, it may also be the printed document, or any other surface bearing an image.

The light diffuser 4 is positioned between the illuminator array 1 and the image bearing surface 10. The light diffuser 4 is positioned with respect to the illuminator array 1 to receive the light beams emitted by the illuminated elements of the illuminator array 1. The light diffuser 4 homogenizes and directionally shapes the light beams coming from the illuminated elements preferably with high-transmission efficiency. The light diffuser can be made of any light-diffusive material, such as polycarbonate or other plastic material. In one embodiment, the light diffuser, for e.g., 60°×1°, is used. The 60°×1° nomenclature specifies the angles of diffusion in two perpendicular directions. There are a variety of angles of diffusion that can be specified for the two directions. The "60" degree diffusion is oriented in the fast scan direction (which is also the linear direction of the illuminator array), and the "1" degree diffusion is oriented in the slow scan direction. Any high ratio of diffusion in the fast scan direction to diffusion in the low scan direction may be used. For example, ratios of 10°:1°, 20°:1°, 30°:1° or higher, including the exemplary 60°:1° may be used. Suitable diffusers of this type which are used in the current system are available as LSD® Light Shaping Diffusers from Physical Optics Corp.

Other factors, such as the distance of the light diffuser 4 from the LED array 1, and/or the orientation of the diffusing surface of the diffuser relative to the LED are taken into account to reduce the diffuse to specular non-uniformity. For example, in one embodiment, a distance of about 5 mm (for the 60°×1° diffuser) was maintained between the LED array 1 and the diffuser 4. For example, in one embodiment, the diffusing surface faces the illuminator array.

The lens array 3, such as a Selfoc® lens or other micro lens arrangement with a predetermined acceptance angle α, is interposed between the image bearing surface 10 and the sensor array 2. A Selfoc® lens is a gradient index lens which consists of fiber rods with parabolic index profile. In one embodiment, the Selfoc® lens has an acceptance angle α of about ±9 degrees.

Figure 14:
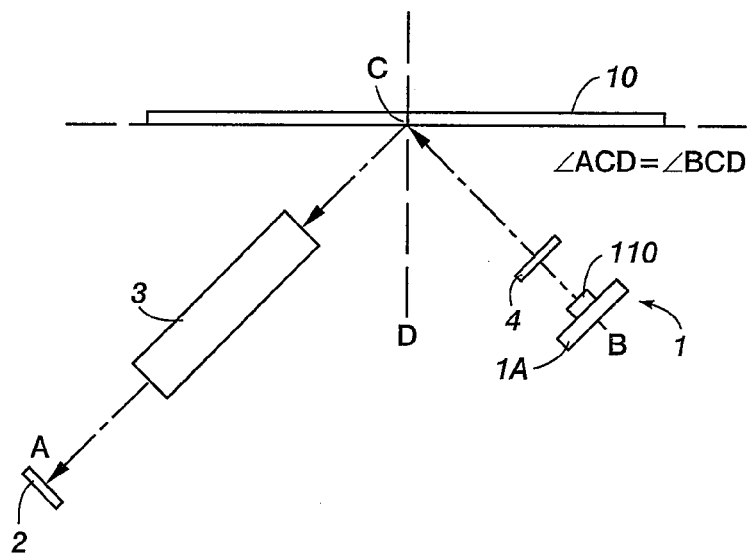
FIG. 14 shows a system in a printer having an illuminator, a light diffuser, and a sensor.

FIG. 14 shows a schematic illustration of the LED illumination system for a specular-mode imager using a light diffuser. As mentioned above, the system has an illuminator array 1, a light diffuser 4, a lens array 3, and a sensor array 2. In one embodiment, the LEDs 110 are placed on a board 1A.

The illuminator array 1 is located on a line B-C and is configured to emit a light beam that passes through the light diffuser 4. The light diffuser 4 is also located on the line B-C. The light beams from the light diffuser 4 are incident onto the image bearing surface 10 at point C, which is reflected, thereby producing generally specular reflectance in a first direction along line C-A, and some generally diffuse reflectance at least. The angle (∠ACD) between line A-C and normal line D-C is substantially equal to the angle (ϕBCD) between line B-C and normal line D-C, such that the illuminator array 1 is configured to emit a light beam onto the image bearing surface 10 at point C, thereby producing a generally specular reflectance from the image bearing surface 10 at a specular reflectance angle along line A-C. The linear sensor array 2 is positioned adjacent to the image bearing surface 10 and is located along line A-C, such that it captures the generally specular portion and the generally diffuse portion of the diffused light beam reflecting off the image bearing surface 10 at a specular reflectance angle at point C. This embodiment provides full resolution images for both types of reflected light. A calibration procedure could be determined so that the signals from the linear sensor array 2 can be used to work out the true specular reflectance and the difference between the specular and diffuse reflectances of the image being measured. For example, the amount of diffuse light being reflected at the specular angle is determined and the subsequent specular sensor readings are corrected by subtracting a fraction of the diffuse sensor signal from the specular sensor signal as discussed in U.S. patent application (Ser. No. 11/944,243), herein incorporated by reference. Line C-D represents a normal line to the surface at a point C of the image bearing surface 10. Point C may actually be a line or a region on the surface of the image bearing surface 10.

Preferably, the linear array sensor is, for example, a full width array (FWA) sensor. A full width array sensor is defined as a sensor that extends substantially an entire width (perpendicular to a direction of motion) of the moving image bearing surface. The full width array sensor is configured to detect any desired part of the printed image, while printing real images. The full width array sensor may include a plurality of sensors equally spaced at intervals (e.g., every 1/600th inch (600 spots per inch)) in the cross-process (or fast scan) direction. See for example, U.S. Pat. No. 6,975,949, incorporated herein by reference. It is understood that other linear array sensors may also be used, such as contact image sensors, CMOS array sensors or CCD array sensors.

In one embodiment, the sensor array 2 includes a specular reflectance sensor array and a diffuse reflectance sensor array as discussed in detail in U.S. patent application (Ser. No. 11/783,174), herein incorporated by reference.

Figure 3:
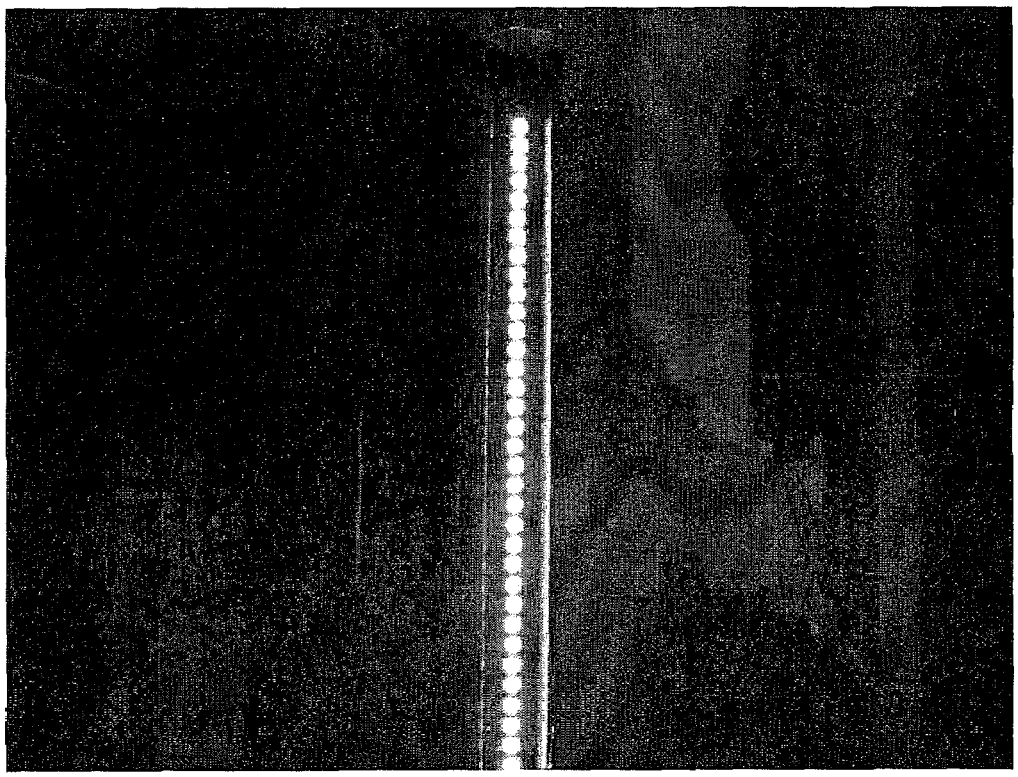
FIG. 3 is a view of the LED illumination system without a light diffuser.
Figure 4:
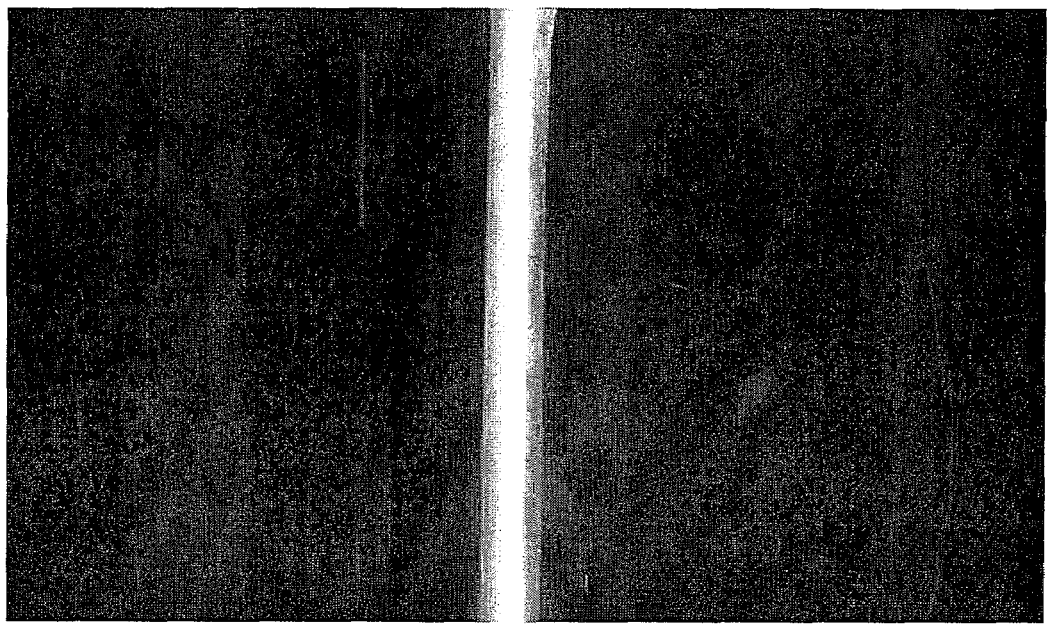
FIG. 4 is a view of the LED illumination system with the light diffuser.

FIGS. 3 and 4 show the illuminator array without and with a light diffuser. As shown in the FIG. 4, when the light diffuser 4 is placed on top of the light emitting diodes 110, a fairly homogenized irradiance is obtained, particularly in the linear direction of the illuminator array. The light diffuser 4 homogenizes or makes more uniform any non-uniformity from the spacing of LEDs 110 (e.g., areas where the LEDs are very close and overlapping light beams are concentrated, or areas where the LEDs are so far apart that darker regions are noticeable). The particular diffuser used, for example, in this present disclosure is a Light Shaping Diffuser (LSD), which is discussed in detail earlier. Plastic or ground glass diffusers could be used as well, the choice of diffuser is dependant on the use and other parameters of a system, such as the distance of the diffuser from the illumination array. As discussed earlier, the position of the light diffuser 4 from the LEDs 110 optimizes homogenization of the light reaching the image bearing surface 10 (as shown in FIGS. 1 and 2).

FIGS. 5A-5C and FIGS. 6A-6B show Fast Fourier Transform (FFT) representation of the measured values that are obtained from raw profiles sensed by the sensor in the image input module. The streak-correction system may be operated in a special mode so that measured values can be obtained from the raw profiles as sensed by the sensor. In contrast, FIGS. 8A-8D show Fast Fourier Transform (FFT) representation of the measured values that are obtained from the print profiles for the streak correction system. In FIGS. 8A-8D, the measured values are obtained from a xerographic print. Hence the scale of the amplitude in FIGS. 5A-5C and FIGS. 6A-6B, is different from the scale of the amplitude in FIGS. 8A-8D.

Figure 5A:
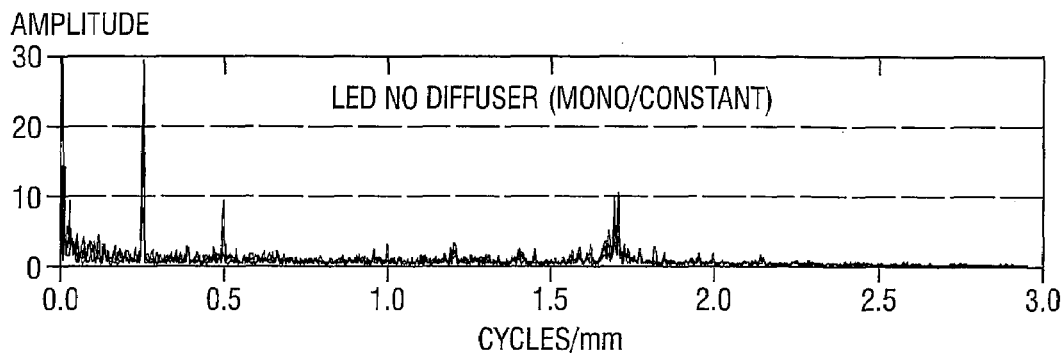
FIGS. 5A-5C show graphs for mono color mode illustrating the amplitude of the Fast Fourier Transform (FFT) of the specular reflectance profile for an LED illumination system without a light diffuser, an LED illumination system with a light diffuser, and a lamp-based illumination system.
Figure 5B:
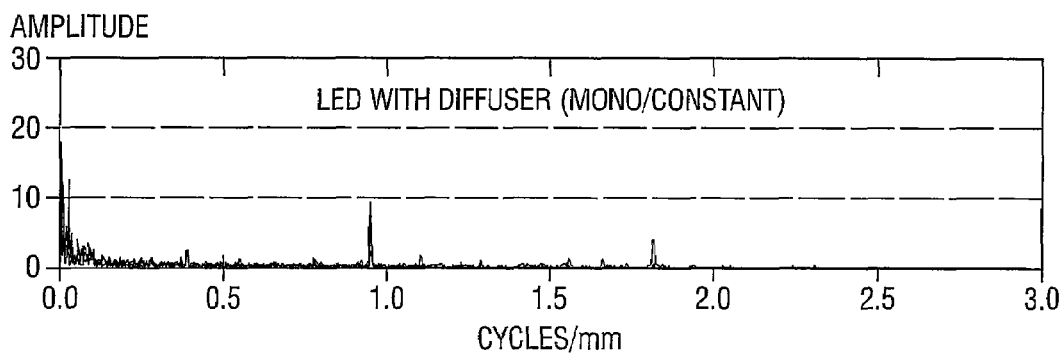
Figure 5C:
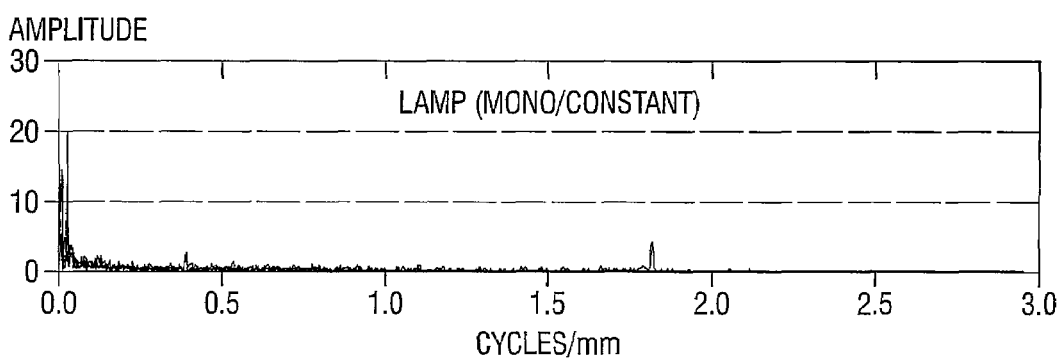

FIGS. 5A-5C show graphs for mono color mode illustrating the amplitude of the Fast Fourier Transform (FFT) of the specular reflectance of an LED illumination system without a light diffuser, an LED illumination system with a light diffuser, and a lamp-based illumination system respectively. The graphs illustrate the spatial frequency in cycles/millimeters on a horizontal x-axis. On a vertical y-axis, the graphs illustrate amplitude of the Fast Fourier Transform (FFT) of the spectral reflectance, which is represented as a normalized reflectance value. As shown in FIG. 5A, the spikes in the profiles is due to various factors, such as LED frequency, Selfoc® frequency etc. The amplitude of the Fast Fourier Transform (FFT) of the spectral reflectance in the plots shown in FIGS. 5B and 5C appear to be same for the LED with the diffuser and for the lamp. By comparing FIGS. 5A and 5B, the spikes in the FFT profiles due to LED frequency and/or Selfoc® frequency (approximately 0.25 and 0.5 cycles/mm, respectively) were reduced or eliminated by use of a light diffuser.

Figure 6A:
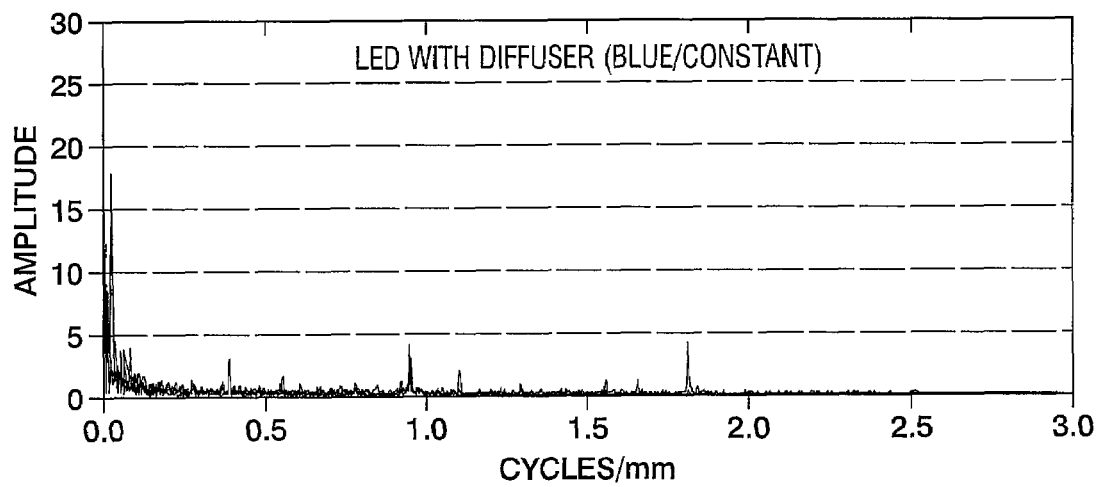
FIGS. 6A-6B show graphs for blue color mode illustrating the amplitude of the Fast Fourier Transform (FFT) of the specular reflectance profile for an LED illumination system with the light diffuser and a lamp-based illumination system.
Figure 6B:
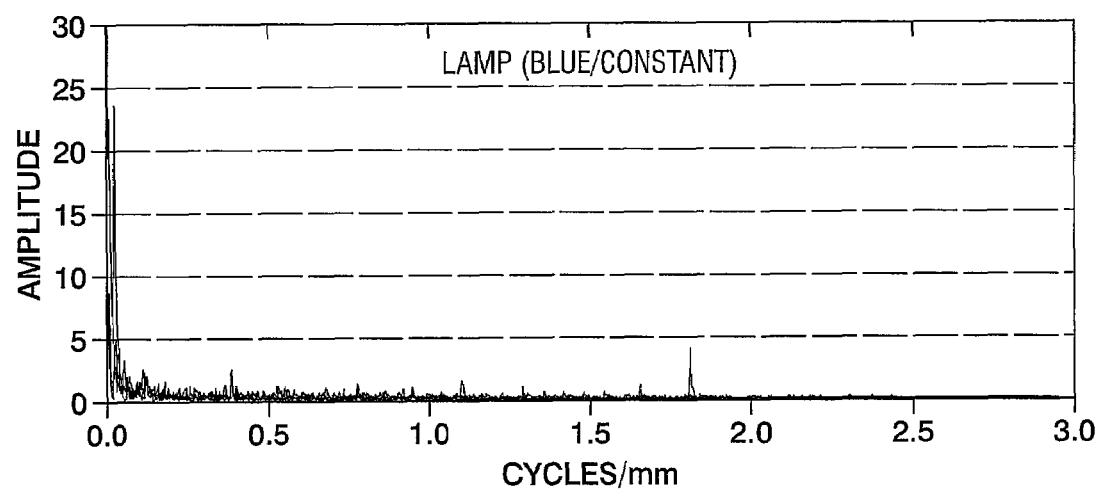

FIGS. 6A-6B show graphs for blue color mode illustrating the amplitude of the Fast Fourier Transform (FFT) of the specular reflectance for an LED illumination system with the light diffuser and a lamp-based illumination system. The graphs illustrate the spatial frequency in cycles/millimeters on a horizontal x-axis. On a vertical y-axis, the graphs illustrate amplitude of the Fast Fourier Transform (FFT) of the spectral reflectance, which is represented as a normalized reflectance value. The amplitude of the Fast Fourier Transform (FFT) of the spectral reflectance in the plots shown in FIGS. 6A and 6B appear to be same for the LED illumination system with the diffuser and for the lamp-based illumination system.

Figure 7:
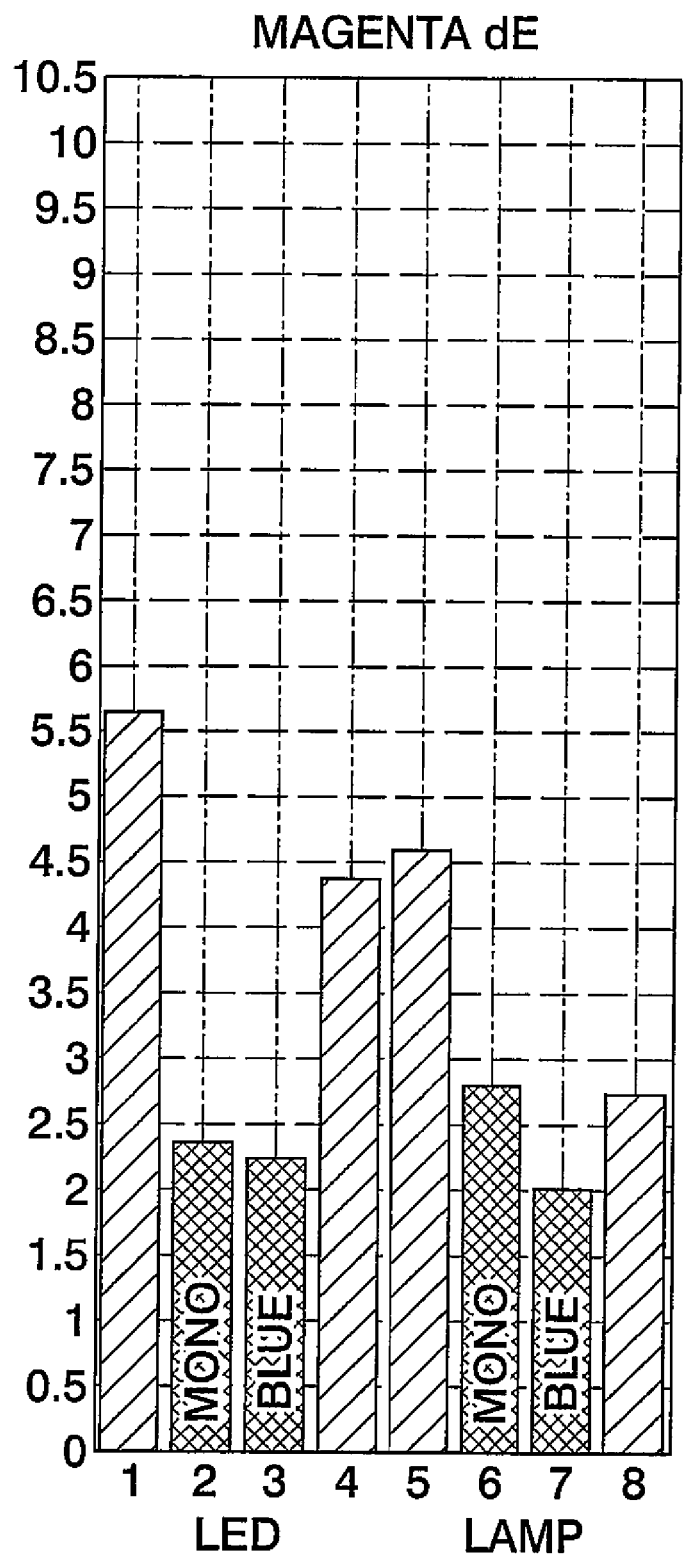
FIGS. 7-9 show bar graphs for full page half tone delta-E results for magenta, yellow and black colors.
Figure 8:
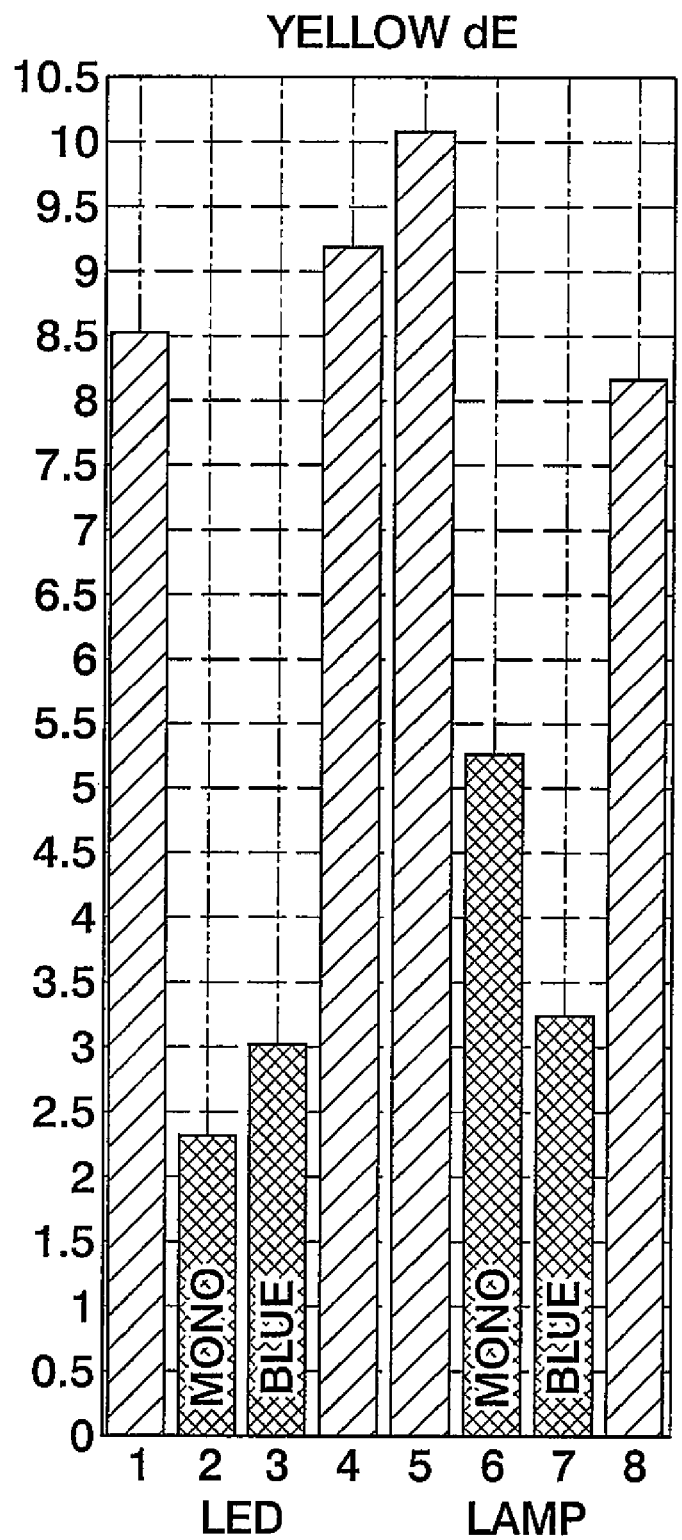
Figure 9:
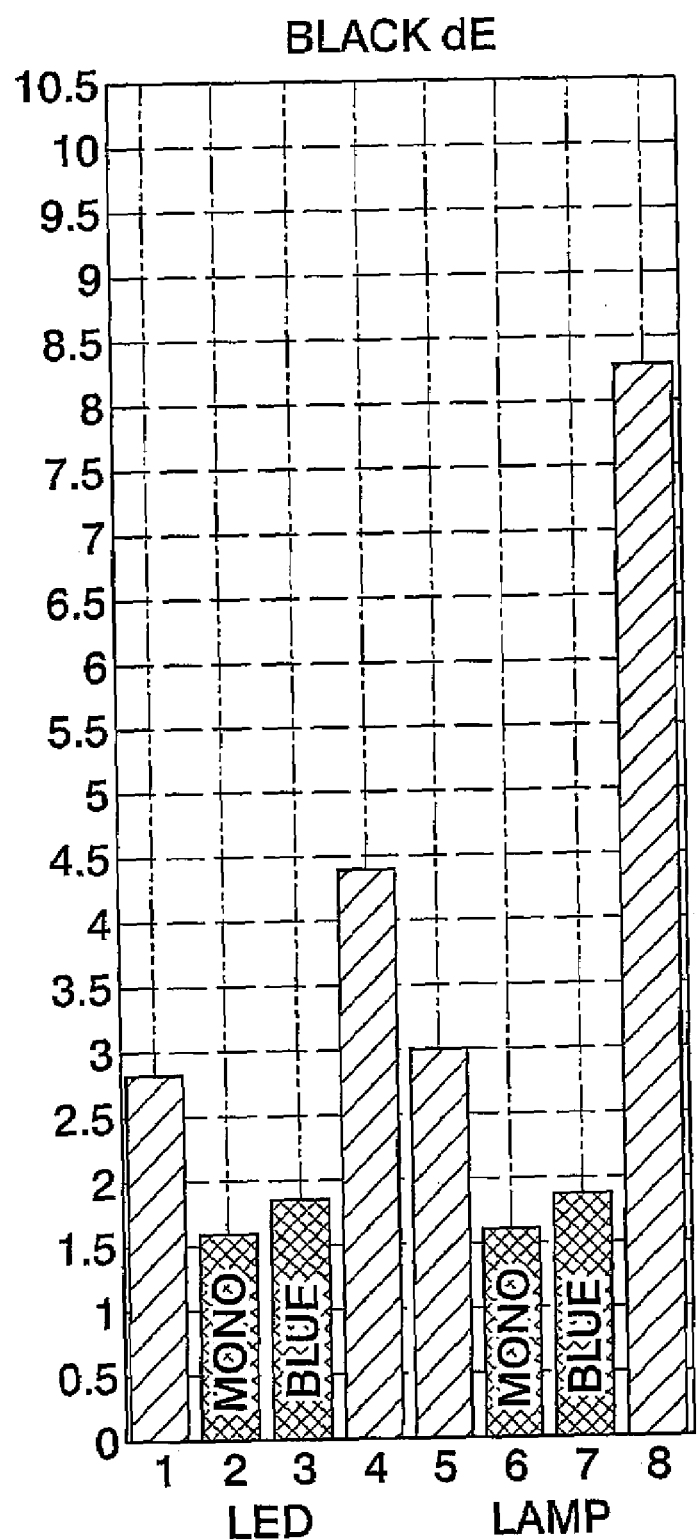

FIGS. 7-9 show bar graphs for full page half tone delta-E results for magenta, yellow and black colors. A spectrophotometer measures color and provides the results of the measurements in a format known as L*a*b* or, more simply, Lab. L*a*b* is a three-dimensional color space where L* is the luminance of the sample, and a* and b* are the color components of the sample. If a* and b* are both zero, the result is a neutral color. If two colors are measured using a densitometer and the L*a*b* values are plugged into the following formula:

$$dE^2 = (L1-L2)^2 + (a1-a2)^2 + (b1-b2)^2$$

The resulting number is referred to as Delta-E or the color difference.

As shown in FIGS. 7-9, the bar graphs illustrate the cells of a test matrix on a horizontal x-axis. On a vertical y-axis, the bar graphs illustrate Delta-E values. In the bar graphs, the mono channel responds to light of all wavelengths, while the blue channel responds only to light near 450 nanometers. As shown in the TABLE 1, the test matrix includes cells 1-8. The cells 1, 4, 5 and 8 are the cells where the streak-correction system of the printer is turned off. The cell 2 is the cell where the streak-correction system is turned on, the color mode is mono and the illuminator used is the plurality of LEDs. The cell 3 is the cell where the streak-correction system is turned on, the color mode is blue and the illuminator used is the plurality of LEDs. The cell 6 is the cell where the streak-correction system is turned on, the color mode is mono and the illuminator used is the lamp. The cell 7 is the cell where the streak-correction system is turned on, the color mode is blue and the illuminator used is the lamp. As shown in FIG. 7, the performance of the LED in magenta delta-E plot was comparable to the performance of the rare gas lamp. As shown in FIG. 8, the performance of the LED in yellow delta-E plot was an improvement over the performance of the rare gas lamp for mono mode, and the performance of the LED in yellow delta-E plot was slightly better than the performance of the rare gas lamp for blue mode. As shown in FIG. 9, the performance of the LED in black delta-E plot was comparable to the performance of the rare gas lamp, with the performance slightly better in the mono mode than in the blue mode.

TABLE 1

| Cell | Illuminator | Streak Correction System | Color Mode |
|---|---|---|---|
| 1 | LED | OFF | MONO |
| 2 | LED | ON | MONO |
| 3 | LED | ON | BLUE |
| 4 | LED | OFF | BLUE |
| 5 | Lamp | OFF | MONO |
| 6 | Lamp | ON | MONO |
| 7 | Lamp | ON | BLUE |
| 8 | Lamp | OFF | BLUE |

Figure 10:
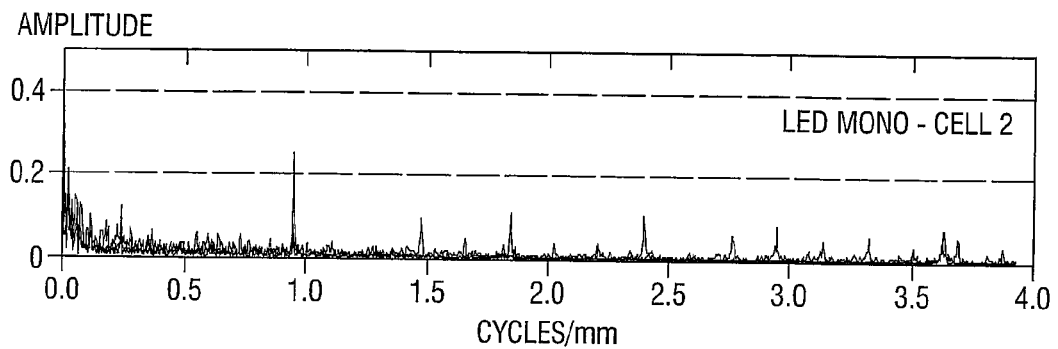
FIGS. 10-13 show graphs for mono color mode and blue color mode for the LED illumination system with the light diffuser and the lamp-based illumination system as obtained from full page half tone delta-E results.
Figure 11:
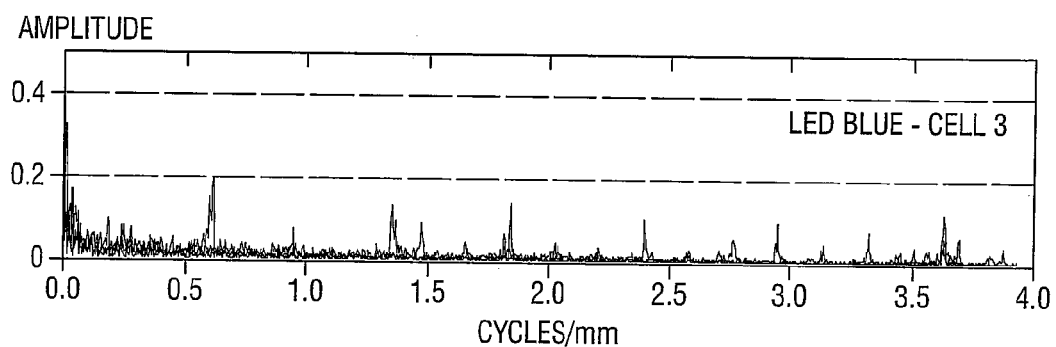
Figure 12:
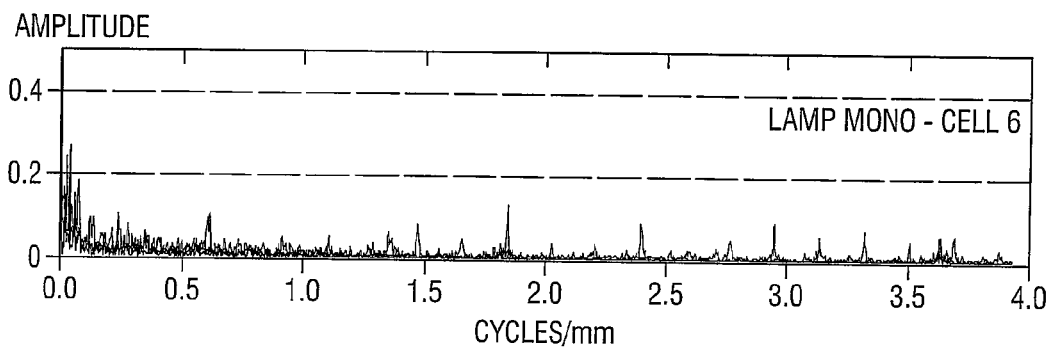
Figure 13:
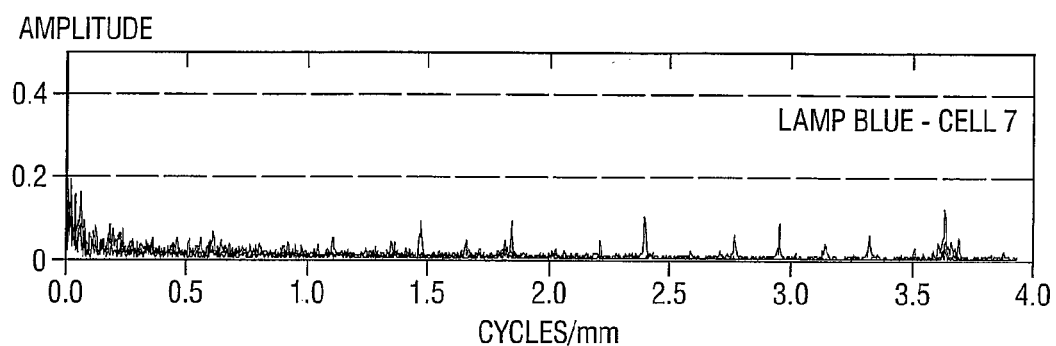

FIGS. 10-13 show graphs for mono color mode and blue color mode illustrating the amplitude of the Fast Fourier Transform (FFT) of the L* profile of a xerographic print for an LED illumination system with the light diffuser and a lamp-based illumination system. These graphs are another representation of the values obtained from full page half tone delta-E results that are also shown in FIGS. 7-9. The graphs illustrate the spatial frequency in cycles/millimeters on a horizontal x-axis. On a vertical y-axis, the graphs illustrate amplitude of the spectral reflectance, which is measured in as a normalized reflectance value. The amplitude of the Fast Fourier Transform (FFT) of the L* profile of a xerographic print in the plots shown in FIGS. 10 and 12 is roughly the same for the LED illumination system with the diffuser and for the lamp-based illumination system in mono color mode. Similarly, the amplitude of the Fast Fourier Transform (FFT) of the L* profile of a xerographic print in the plots shown in FIGS. 11 and 13 is roughly the same for the LED illumination system with the diffuser and for the lamp-based illumination system in the blue color mode.

A processor (not shown) is provided to both calibrate the sensor and to process the reflectance data detected by the linear sensor. It could be dedicated hardware like ASICs or FPGAs, software, or a combination of dedicated hardware and software. For the different applications the basic algorithm for extracting the specular and diffuse components would be the same but the analysis for the particular applications would vary.

Figure 15:
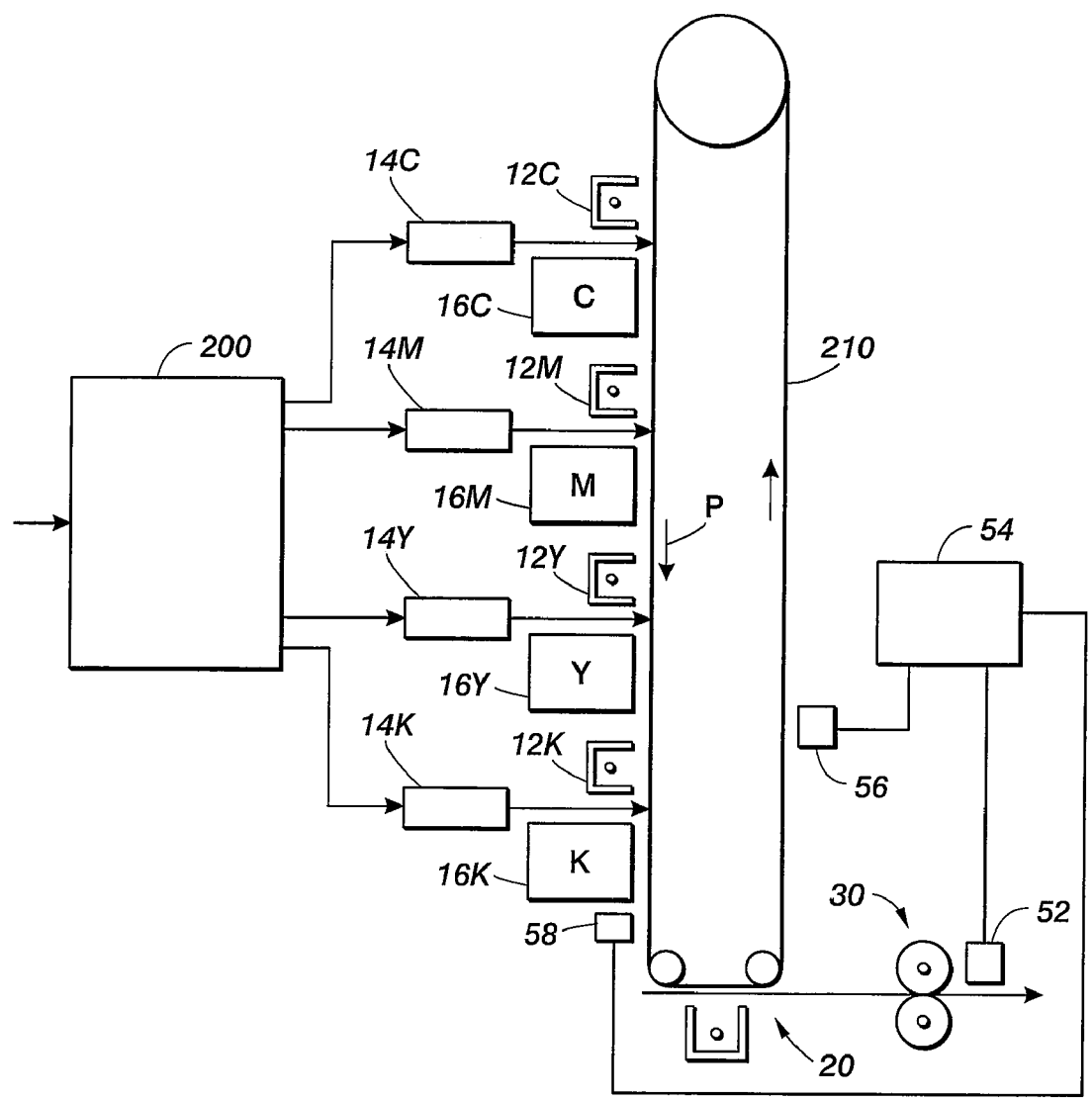
FIG. 15 is a simplified elevational view of basic elements of a xerographic color printer, showing a context of the various embodiments.

FIG. 15 is a simplified elevational view of basic elements of a color printer, showing a context of the present disclosure. Specifically, there is shown an "image-on-image" xerographic color printer, in which successive primary-color images are accumulated on a photoreceptor belt, and the accumulated superimposed images are in one step directly transferred to an output sheet as a full-color image. In one implementation, the Xerox Corporation iGen3® digital printing press may be utilized. However, it is appreciated that any printing machine, such as monochrome machines using any technology, machines which print on photosensitive substrates, xerographic machines with multiple photoreceptors, or ink-jet-based machines, can beneficially utilize the present disclosure as well.

Specifically, the FIG. 15 embodiment includes a belt photoreceptor 210, along which are disposed a series of stations, as is generally familiar in the art of xerography, one set for each primary color to be printed. For instance, to place a cyan color separation image on photoreceptor 210, there is used a charge corotron 12C, an imaging laser 14C, and a development unit 16C. For successive color separations, there is provided equivalent elements 12M, 14M, 16M (for magenta), 12Y, 14Y, 16Y (for yellow), and 12K, 14K, 16K (for black). The successive color separations are built up in a superimposed manner on the surface of photoreceptor 210, and then the combined full-color image is transferred at transfer station 20 to an output sheet. The output sheet is then run through a fuser 30, as is familiar in xerography.

Also shown in the FIG. 15 is a set of what can be generally called "monitors," such as 50 and 52, which can feed back to a control device 54. The monitors such as 50 and 52 are devices which can make measurements to images created on the photoreceptor 210 (such as monitor 50) or to images which were transferred to an output sheet (such as monitor 52). These monitors can be in the form of optical densitometers, calorimeters, electrostatic voltmeters, etc. There may be provided any number of monitors, and they may be placed anywhere in the printer as needed, not only in the locations illustrated. The information gathered therefrom is used by control device 54 in various ways to aid in the operation of the printer, whether in a real-time feedback loop, an offline calibration process, a registration system, etc.

Typically, a printer using control systems which rely on monitors such as 50, 52 require the deliberate creation of what shall be here generally called "test patches" which are made and subsequently measured in various ways by one or another monitor. These test marks may be in the form of test patches of a desired darkness value, a desired color blend, or a particular shape, such as a line pattern; or they may be of a shape particularly useful for determining registration of superimposed images ("fiducial" or "registration" marks). Various image-quality systems, at various times, will require test marks of specific types to be placed on photoreceptor 210 at specific locations. These test marks will be made on photoreceptor 210 by one or more lasers such as 14C, 14M, 14Y, and 14K. Printing process may be controlled, for example, by a print controller 200.

As is familiar in the art of "laser printing," by coordinating the modulation of the various lasers with the motion of photoreceptor 210 and other hardware (such as rotating mirrors, etc., not shown), the lasers discharge areas on photoreceptor 210 to create the desired test marks, particularly after these areas are developed by their respective development units 16C, 16M, 16Y, 16K. The test marks must be placed on the photoreceptor 210 in locations where they can be subsequently measured by a (typically fixed) monitor elsewhere in the printer, for whatever purpose.

In an embodiment, the linear sensor array 2, as described above, can be placed just before or just after the transfer station 20 where the toner is transferred to the sheet, for example, on monitors such as 50, 56. In another embodiment, the linear sensor array 2, may be placed directly on a printed sheet as the printed sheet comes out of the machine, for example, on monitor such as 52.

While the specific embodiments of the present disclosure have been described above, it will be appreciated that the disclosure may be practiced otherwise than described. The description is not intended to limit the disclosure.

What we claim is:

1. A system for detecting reflectance from an image bearing surface in a printer or electronic copier, comprising:
    an illuminator array positioned adjacent to the image bearing surface, the illuminator array comprising a plurality of discrete illuminator elements spaced in a linear arrangement, the illuminating elements each being configured to emit a light beam for transmission to the image bearing surface at an incidence angle;
    a light diffuser positioned between the illuminator array and the image bearing surface, the light diffuser being positioned with respect to the illuminator array to receive the light beams emitted by the illuminator elements and to diffuse the light beams being transmitted to the image bearing surface in the linear direction of the illuminator array;
    a linear sensor array comprising a plurality of sensors positioned adjacent to the image bearing surface such that specular and diffuse portions of the light beams reflecting off the image bearing surface at a reflectance angle are received by the sensors.

2. The system of claim 1, wherein the illuminator array comprises a linear LED array, wherein each discrete illuminator comprises an LED.

3. The system of claim 1, wherein the image bearing surface is on a photoreceptor comprising a belt or a drum.

4. The system of claim 1, further comprising a lens placed in the optical path of the light beams reflecting off the image bearing surface at the reflectance angle.

5. The system of claim 4, wherein the lens is a gradient index lens.

6. The system of claim 1, wherein the linear sensor array is a full width array (FWA) sensor, contact image sensor, a CMOS array sensor or a CCD array sensor.

7. The system of claim 1, further comprising a processor configured to process the specular and the diffuse portions of the light beams reflecting off the image bearing surface and detected by the linear sensor array.

8. A method for detecting reflectance from an image bearing surface in a printer or electronic copier, the method comprising:
    positioning an illuminator array comprising a plurality of discrete illuminator elements spaced in a linear arrangement adjacent to the image bearing surface and configuring the illuminator elements to emit a light beam for transmission to the image bearing surface at an incidence angle;
    positioning a light diffuser between the illuminator array and the image bearing surface;
    positioning the diffuser with respect to the illuminator array to receive the light beams emitted by the illuminator elements and to diffuse the lights beams being transmitted to the image bearing surface in the linear direction of the illuminator array;
    positioning a linear sensor array comprising a plurality of sensors adjacent to the image bearing surface, such that specular and diffuse portions of the light beams reflecting off the image bearing surface at a reflectance angle are received by the sensors.

9. The method of claim 8, further comprising processing the specular and the diffuse portions of the light beams reflecting off the image bearing surface and detected by the linear sensor array.

10. The method of claim 8, wherein the illuminator array comprises a linear LED array, wherein each discrete illuminator comprises an LED.

11. The method of claim 8, wherein the image bearing surface is on a photoreceptor comprising a belt or a drum.

12. The method of claim 8, further comprising using a lens placed in the optical path of the light beams reflecting off the image bearing surface at the reflectance angle.

13. The method of claim 12, wherein the lens is a gradient index lens.

14. The method of claim 8, wherein the linear sensor array is a full width array (FWA) sensor, contact image sensor, a CMOS array sensor or a CCD array sensor.

* * * * *